United States Patent
Gambarini et al.

[11] Patent Number: 5,816,808
[45] Date of Patent: Oct. 6, 1998

[54] INSTRUMENT FOR PERIODONTIC TREATMENT AND RELATED METHOD

[75] Inventors: Gianluca Gambarini, Rome; Paolo Trisi, Pescara; Antonio Scarano, Collecorvino, all of Italy; Jean-Marie Badoz, Pontarlier, France

[73] Assignee: Micro Mega International Manufactures S.A., Besancon, France

[21] Appl. No.: 596,265

[22] PCT Filed: Jun. 20, 1995

[86] PCT No.: PCT/FR95/00820

§ 371 Date: Apr. 8, 1996

§ 102(e) Date: Apr. 8, 1996

[87] PCT Pub. No.: WO95/35068

PCT Pub. Date: Dec. 28, 1995

[30] Foreign Application Priority Data

Jun. 20, 1994 [IT] Italy ............................ MI94 A 001286

[51] Int. Cl.⁶ ..................................................... A61C 3/03
[52] U.S. Cl. .......................... 433/166; 433/119; 433/142
[58] Field of Search .................................. 433/102, 118, 433/119, 125, 142, 143, 165, 166, 216; 132/321, 329

[56] References Cited

U.S. PATENT DOCUMENTS

| 251,598 | 12/1881 | Johanson | 433/102 |
|---|---|---|---|
| 4,526,541 | 7/1985 | Hubschmid | 433/165 |
| 4,608,019 | 8/1986 | Kumabe et al. | 433/118 |
| 4,731,019 | 3/1988 | Martin | 433/119 |
| 4,824,370 | 4/1989 | Laurichesse et al. | 433/102 |
| 5,158,457 | 10/1992 | Meier et al. | 433/118 |
| 5,236,358 | 8/1993 | Sieffert | 433/119 |

FOREIGN PATENT DOCUMENTS

| 670756 | 7/1989 | Switzerland | 433/102 |
|---|---|---|---|
| 2018603 | 10/1979 | United Kingdom | 433/142 |

*Primary Examiner*—Ralph A. Lewis
*Attorney, Agent, or Firm*—Weiser and Associates, P.C.

[57] ABSTRACT

The invention relates to an instrument for periodontal treatment, consisting of a connection piece (4) and of a blade (1), wherein said blade (1) has an abrasive part exhibiting two sectors (10, 11) distributed along the blade, and each situated on opposite sides of a plane passing through the axis of the blade, these two sectors (10, 11) exhibiting different levels of abrasiveness such that when the instrument is introduced into the periodontal pocket during treatment, the more abrasive sector comes into contact with the root surface of the tooth, and the other, less abrasive, sector comes into contact with the mucosa, said instrument being adapted to be held by way of its connection piece (4) on a handpiece which confers a vibratory movement on it, allowing the two sectors (10, 11) to effect the detachment of the undesirable tartar.

17 Claims, 1 Drawing Sheet

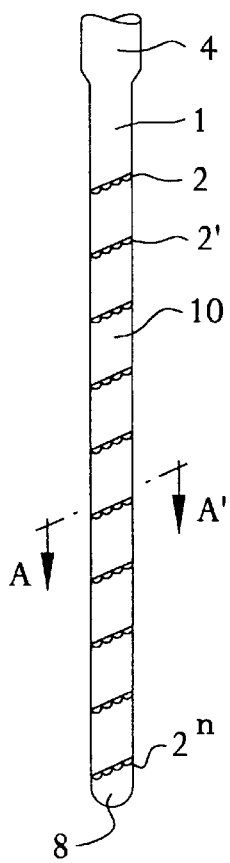
FIG. 1
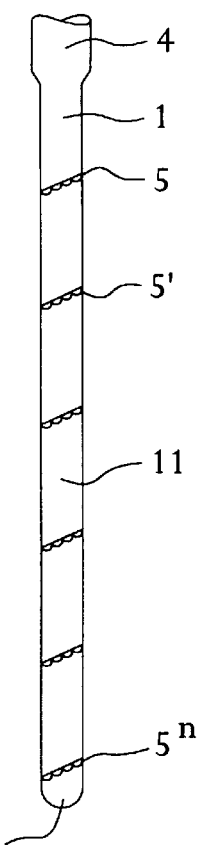
FIG. 2
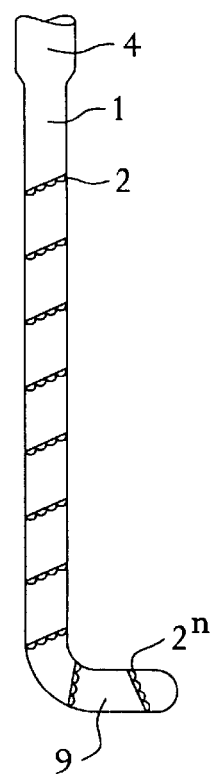
FIG. 4
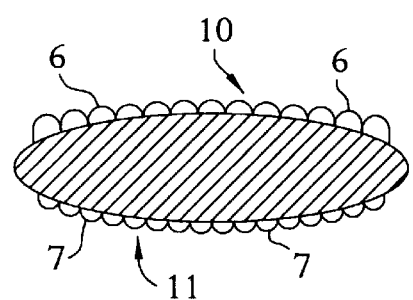
FIG. 3
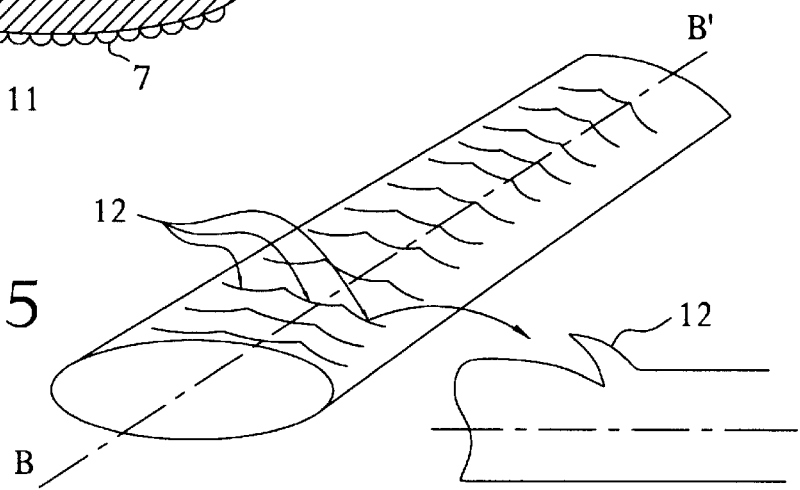
FIG. 5
FIG. 6

INSTRUMENT FOR PERIODONTIC TREATMENT AND RELATED METHOD

BACKGROUND OF THE INVENTION

1. Field of the Invention

The present invention relates to the field of instruments for periodontal treatment, and in particular instruments which permit removal of tartar simultaneously from the root surface and from the mucosal wall in the periodontal pockets.

2. Description of the Related Art

The success of periodontal treatment depends to a great extent on the complete elimination of the tartar which is situated in the periodontal pockets.

It is known that the root surfaces of the teeth affected by periodontolysis in the active phase are covered with a bacterial plaque and tartar within the depth of the alveolus, for which reason the root surface is found to be damaged and the cementum necrosed. By removing the plaque, the tartar and the necrosed cementum, it is possible to restore a biological gingival seal which maintains the periodontium in a healthy state.

The means known at the present time are, on the one hand, manual curettes, or else inserts which are mounted on vibratory handpieces, in particular ultrasonic scalers. Disadvantages of these means are that the rigidity of the instruments does not permit treatment of the deep periodontal pockets and does not permit satisfactory cleaning of the furcations. This forces the practitioner to operate in accordance with the conventional methods of periodontal surgery, which involves the cutting of flaps.

SUMMARY OF THE INVENTION

The object of the present invention is to provide instruments and a method for treating periodontal disease, permitting treatment of the deep periodontal pockets and the furcation zones without having to resort to the cutting of flaps.

More precisely, the invention relates to an instrument for periodontal treatment, consisting of a handle (i.e., connection piece) and of a blade, wherein said blade has an active (i.e., abrasive) part exhibiting two sectors distributed along the blade, and each situated on either side (i.e., opposite sides) of a plane passing through the axis of the blade, these two sectors exhibiting different levels of aggressiveness (i.e., abrasiveness) such that when the instrument is introduced into the periodontal pocket during treatment, the more abrasive sector comes into contact with the root surface of the tooth, and the other, less abrasive, sector comes into contact with the mucosa, said instrument being held by way of its connection piece on a handpiece which confers a vibratory movement on it, allowing the two sectors to effect the detachment of the undesirable tartar.

The instrument for dental surgery according to the present invention has the advantage that once it has been introduced into the periodontal alveolus, it can reach depths which are inaccessible to the instruments according to the prior art.

Another advantage afforded by the instrument according to the present invention is the fact that when it is being used, the root surface on the one hand and the mucosal wall on the other hand are both treated simultaneously.

BRIEF DESCRIPTION OF THE DRAWINGS

Other advantages and characteristics of the instrument for dental surgery according to the present invention will become clear to specialists in the field from the following detailed description of two illustrative embodiments, with reference being made to the attached drawing, in which:

FIG. 1 represents a side elevation of the instrument,

FIG. 2 represents a side elevation, from the opposite side in relation to FIG. 1, FIG. 3 represents an enlarged cross section along the line A—A' in FIG. 1, and FIG. 4 represents a side elevation of a second embodiment of the instrument, FIG. 5 represents a perspective view of a variant of the invention, FIG. 6 represents an enlarged cross section along the line B—B' in FIG. 5.

DESCRIPTION OF THE PREFERRED EMBODIMENT(S)

Referring to FIG. 1, it can be seen that the instrument for dental surgery according to the present invention consists in the main of a blade (1) having a substantially elliptical cross section, and exhibiting, on its side, a plurality of mutually adjacent projections which give it the desired roughness. These projections are disposed in parallel lines (2, 2', etc . . . ) which are preferably inclined with respect to the plane perpendicular to the axis of the instrument. Their inclination can vary within fairly wide limits, although it can also be nil.

The vertical distance between each line (2) and the line adjacent to it can be between 0.25 and 2 cm, preferably between 0.5 and 1 cm.

The projections which form the lines (2) project. laterally from the side of the instrument (1) by preferably approximately 0.05 mm.

The blade (1) has, at one end, the connection piece (4) for joining it to the appliance used to operate the instrument. The total length of this instrument is similar to that of the known endodontic files, that is to say approximately 12 to 25 mm. The thickness of the blade (1) can be between 0.1 and 3 mm, and its width between 0.2 and 3.5 mm.

In order to operate the instrument, it is possible to use any appliance provided for this purpose, although it is preferable to use ultrasound generators. The reason for this is that ultrasonic vibrations have intrinsic antibacterial properties and they are at the same time capable of detaching tartar residues from the root wall. In addition, by means of these vibrations, the appliance is able to reach and to file even the most inaccessible zones of the alveolus, without damaging the connective tissue which surrounds it.

Referring to FIG. 2, it can be seen that the other side of the blade (1) also exhibits a plurality of parallel lines (5, 5', etc...) of projections. What has just been stated in respect of the lines (2, 2', etc . . . ), with reference to FIG. 1, applies to the inclination of these lines (5, 5', etc). There are differences, however, as regards the vertical distance between the lines (5, 5') and the dimensions of the projections. The distance between a line (5) and the line adjacent to it is greater than the distance between the lines (2), preferably equal to approximately twice the distance. By contrast, the dimensions of the projections (7) which form the lines (5) are smaller than those of the projections (6) which form the lines (2), and they are preferably equal to approximately half the size of these.

FIG. 3 shows the profiles of the projections (6) which form the lines (2) and the profiles of the projections (7) which form the lines (5). The projections (6) have a substantially semicircular profile and they join gradually to the surface of the blade (1). Each of these projections is cut, by machining with a suitable tool, from the side (10) of the blade (1). The radius of each semicircle is preferably between approximately 50 and 500μ. The projections (6) are intended to come into contact with the root surface of the tooth when the instrument is in use. The vibration of the instrument applied against this surface instigates the removal of the necrosed cementum from the dentine layer reduced to a slurry which forms during treatment.

The projections (7) also have a substantially semicircular profile, like the projections (6), and like the latter they are cut, by machining with a suitable tool, from the other side (11) of the blade (1). The radius of these semicircles is preferably between approximately 25 and 250μ. These projections are intended to come into contact with the surface of the mucosal wall of the periodontal alveoli when the instrument is in use.

The vibration of the instrument thus instigates not only the removal of the necrosed cementum, but also the simultaneous removal of the granular tissue of the mucosal wall of the periodontal alveolus. This removal constitutes one of the aims of effective treatment of the periodontium, so as to obtain healthy tissue which is free from bacteria and which is capable of sealing, by adhesion, the root surface which has been treated.

FIG. 3 also shows that the cross section of the blade (1) has a very flattened elliptical shape which makes it possible to prepare the flat or slightly convex portions of the root wall. This flattened shape also affords the possibility of flexing the instrument during use, in such a way as to adapt it to the curves present in the root furcations, and making it possible to treat zones of the root which cannot be accessed by the instruments according to the prior art.

The instrument according to the present invention can be made of any material suitable for this purpose. It is possible, for example, to use materials employed in the manufacture of curettes. However, it is preferable to use the titanium alloys which have recently been introduced in the manufacture of endodontic files.

FIG. 4 represents a variant of the embodiment in FIG. 1. Whereas the instrument represented in FIG. 1 has a straight and simply rounded tip (8), the instrument which is the subject of the variant in FIG. 4 exhibits a curve at the apex (9), which is similar to that of the known curettes and which permits more effective cleaning of the flat root surfaces within larger alveoli.

FIG. 5 represents another embodiment of the projections which can be in the form of small tongues (12) which are raised like teeth, of the RISPI (trademark) or SHAPER (trademark) type, and of which there are three, for example, on each parallel line, although their number can vary depending on requirements.

Other variants and/or modifications of the embodiments described and illustrated above may be made by specialists in the field without departing from the scope of the present invention. For example, these variants could concern the shape of the blade (1) which, instead of the optimal straight shape, could be narrowed in the direction of the tip in order to adapt it for use within excessively narrow gingival alveoli. Moreover, the blade (1) can have any suitable cross section, for example circular or oblong, and the blade can be cylindrical or conical.

We claim:

1. An instrument for periodontal treatment, consisting of a connection piece (4) and of a blade (1), wherein said blade (1) has an abrasive part exhibiting two sectors (10, 11) distributed along the blade, and each situated on opposite sides of a plane passing through the axis of the blade, these two sectors (10, 11) exhibiting different levels of abrasiveness such that when the instrument is introduced into a periodontal pocket during treatment, the more abrasive sector comes into contact with the root surface of the tooth, and the other, less abrasive, sector comes into contact with the mucosa, said instrument being adapted to be held by way of its connection piece (4) on a handpiece which confers a vibratory movement on it, allowing the two sectors (10, 11) to effect the detachment of the undesirable tartar, wherein the blade (1) has a substantially elliptical cross section and is provided, on one of the sectors (10), with a plurality of adjacent projections (6) which are disposed in first parallel lines (2. 2'), and, on the other sector (1), with a plurality of smaller projections (7) disposed in second parallel lines (5, 5') which are more spaced apart than the first parallel lines (2, 2').

2. The instrument for periodontal treatment as claimed in claim 1, wherein the adjacent projections (6) are small raised tongues (12).

3. The instrument for periodontal treatment as claimed in claim 1, wherein the adjacent projections (6) project by 0.05 mm from the blade (1).

4. The instrument for periodontal treatment as claimed in claim 1, wherein the distance between the first parallel lines (2, 2') is between 0.5 and 1 mm.

5. The instrument for periodontal treatment as claimed in claim 1, wherein the first and second parallel lines (2, 2'; 5, 5') are inclined with respect to the plane perpendicular to the axis of the instrument, and wherein their inclination is between 40° and 50°.

6. The instrument for periodontal treatment as claimed in claim 1, which has, at a tip of the blade, an apical curvature (9).

7. The instrument for periodontal treatment as claimed in claim 1, wherein the abrasive sector (10) is formed on a distal part of the blade (1), a tip of the blade remaining non-abrasive.

8. The instrument for periodontal treatment as claimed in claim 1, wherein the blade (1) has an oblong cross section.

9. An instrument for periodontal treatment, comprising:
   (a) a connection piece, adapted to be held on a handpiece that confers a vibratory movement to the instrument; and
   (b) a blade, connected at one end to the connection piece, wherein the blade has a set of projections on each of two opposite sides of the blade, wherein the projections on one side of the blade are smaller than the projections on the other side of the blade, such that, when the instrument is introduced into a periodontal pocket during treatment, the side of the blade having larger projections comes into contact with the root surface, and the side of the blade having smaller projections comes into contact with the mucosa, wherein:
   each set of projections is arranged in lines of projections; and
   the distances between adjacent lines of the smaller projections on one side of the blade are greater than the distances between adjacent lines of the larger projections on the other side of the blade.

10. The instrument of claim 9, wherein the lines of projections are inclined with respect to a plane perpendicular to the axis of the instrument.

11. The instrument of claim 9, wherein the blade has an elliptical cross section.

12. The instrument of claim 9, wherein the blade is curved at the end opposite the connection piece.

13. The instrument of claim 9, wherein the projections are small tongues.

14. The instrument of claim 9, wherein the projections are semicircular in cross section.

15. The instrument of claim 9, wherein the blade is smooth at the end opposite the connection piece.

16. The instrument of claim 9, wherein the blade narrows in the direction of the end opposite the connection piece.

17. The instrument of claim 9, wherein:

the lines of projections that are inclined with respect to a plane perpendicular to the axis of the instrument;

the projections are either small tongues or semicircular in cross section; and the blade has an elliptical cross section, is curved and smooth at the end opposite the connection piece, and narrows in the direction of the end opposite the connection piece.

* * * * *